United States Patent
Kok et al.

(10) Patent No.: US 9,896,733 B2
(45) Date of Patent: Feb. 20, 2018

(54) METHOD AND KIT FOR PREDICTION SUCCESS OF IN VITRO FERTILIZATION

(75) Inventors: Dirk Jan Kok, Rotterdam (NL); Jozef Stephanus Elisabeth Laven, Rotterdam (NL); Delshad Mama Maghdid, Rotterdam (NL); Nicole Geertje Maria Beckers, Rotterdam (NL)

(73) Assignee: ARTPRED B.V., 'S-Hertogenbosch (NL)

( * ) Notice: Subject to any disclaimer, the term of this patent is extended or adjusted under 35 U.S.C. 154(b) by 0 days.

(21) Appl. No.: 14/237,396

(22) PCT Filed: Aug. 12, 2011

(86) PCT No.: PCT/NL2011/050563
§ 371 (c)(1),
(2), (4) Date: May 5, 2014

(87) PCT Pub. No.: WO2013/025095
PCT Pub. Date: Feb. 21, 2013

(65) Prior Publication Data
US 2014/0322715 A1    Oct. 30, 2014

(51) Int. Cl.
*C12Q 1/68* (2006.01)
*G01N 33/68* (2006.01)
*C07H 21/02* (2006.01)

(52) U.S. Cl.
CPC .......... *C12Q 1/689* (2013.01); *C12Q 1/6881* (2013.01); *G01N 33/689* (2013.01); *C12Q 2600/16* (2013.01); *G01N 2333/31* (2013.01); *G01N 2333/335* (2013.01)

(58) Field of Classification Search
CPC .. C12Q 1/6881; C12Q 1/689; C12Q 2600/16; G01N 2333/31; G01N 2333/335; G01N 33/689
See application file for complete search history.

(56) References Cited

FOREIGN PATENT DOCUMENTS

| WO | 94/21815 | 9/1994 |
|---|---|---|
| WO | 99/45099 | 9/1999 |
| WO | 2005/093408 | 10/2005 |
| WO | 2008/084105 | 7/2008 |

OTHER PUBLICATIONS

Hyman, R. w. et al., J. Assist. Reprod. Genet., vol. 29, pp. 105-117 (2012).*
Pelzer, E.S. et al., PLoS ONE, vol. 8, e59062, pp. 1-10 (2013).*
International Search Report, PCT/NL2011/050563, dated Apr. 3, 2012, 3 pages.
Selman et al. Examination of bacterial contamination at the time of embryo transfer, and its impact on the IVF/pregnancy outcome. J. Assist Reprod Genet 24 (2007), 395-399.
Moore et al. Bacteria in the transfer catheter tip influence the live-birth rate after in vitro fertilization. Fertility and Sterility 74 (2000) 1118-1124.
Eckert et al. Relationship of vaginal bacteria and inflammation with conception and early pregnancy loss following in-vitro fertilization. Infect Dis Obstet Gynecol 11 (2003), 11-17.
Selim et al. Effective of metronidazole to bacterial flora in vagina and the impact of microbes on live birth rate during intracytoplasmic sperm injection (ICSI). Arch Gynecol Obstet 284 (2011) 1449-1453.
Barnocchi et al. Impact of bacterial contamination assessed at embryo transfer on the pregnancy outcome. Abstracts of the 22nd Annual Meeting of the ESHRE, Prague Czech Republic, Jun. 18-21, 2006,1 page.
Jakobsson and Forsum. Changes in the predominant human *Lactobacillus* flora during in vitro fertilization. Annals of Clinical Microbiology and Antimicrobials 7 (2008) 14: 9 pages.
Capelli et al. Influence of bacterial vaginosis on IVF outcome. Abstracts of the 17th Annual Meeting of the ESHRE, Lausanne, Switzerland 2001, 2 pages.
Cottell et al. Are seminal fluid microorganisms of significance or merely contaminants? Fertility and Sterility 74 (2000), 465-470.
Kusters et al.; "A multiplex real-time PCR assay for routine diagnosis of bacterial vaginosis"; European Journal of Clinical Microbiology and Infectious Diseases; 34(9); pp. 1-8; http://www.ncbi.nlm.nih.gov/pmc/articles/PMC4545173/ (Jul. 5, 2015).
Wood et al.; "Kraken: ultrafast metagenomic sequence classification using exact alignments"; Genome Biology; 15(3): R46; pp. 1-13; http://www.ncbi.nlm.nih.gov/pmc/articles/PMC4053813/ (Mar. 3, 2014).
Budding et al; "IS-pro: high-throughput molecular fingerprinting of the intestinal microbiota"; FASEB Journal; pp. 1-12; http://www.fasebj.org/content/24/11/4556.long (Jul. 19, 2010).

* cited by examiner

*Primary Examiner* — Teresa E Strzelecka
(74) *Attorney, Agent, or Firm* — TraskBritt, P.C.

(57) ABSTRACT

The disclosure provides a method of determining the chance of a successful pregnancy based on the ratio indicated as a formula that uses the presence of *Lactobacillus* and *Staphylococcus* bacteria in relation to the total amount of bacteria in a sample of a subject, preferably a urine sample. Also provided in the disclosure is a kit, preferably a qPCR kit, for performing the method of the disclosure and outputting the result. Such a method and kit are particularly advantageous for predicting the chance of a successful pregnancy in subjects undergoing or eligible for an artificial insemination method such as IVF or ICSI.

9 Claims, No Drawings

METHOD AND KIT FOR PREDICTION SUCCESS OF IN VITRO FERTILIZATION

CROSS-REFERENCE TO RELATED APPLICATION

This application is a national phase entry under 35 U.S.C. § 371 of International Patent Application PCT/NL2011/050563, filed Aug. 12, 2011, designating the United States of America and published in English as International Patent Publication WO 2013/025095 A1 on Feb. 21, 2013.

SEQUENCE LISTING

Applicants incorporate by reference the material contained in the accompanying computer-readable Sequence Listing identified as P95262US00_seqlist_ST25.txt, having a file creation date of Feb. 14, 2014 9:47 A.M. and file size of 3.53 KB.

TECHNICAL FIELD

This application relates to the field of human reproduction, more particularly to situations in which human reproduction is failing. In such a case, artificial methods are in place to assist women in getting pregnant, but the success of these treatments is low and, more importantly, unpredictable. The current disclosure now provides a more reliable method for predicting the chances of success in in vitro fertilization.

BACKGROUND

Sub-fertility affects 10% to 15% of couples in the western world. This sub-fertility can, in half of the cases, be ascribed to female causes, in 20%-26% to male causes, and in 25%-30% the cause is unknown (J. L. Evers, 2002, *Lancet* 360:151-159). Many couples turn to in vitro fertilization (IVF) or intra-cytoplasmatic sperm injection (ICSI) to fulfil their child-wish. The success rate of these techniques is around 25% per started cycle (A. Andersen et al., 2007, *Hum. Reprod* 22:1513-1525). It would be of great emotional and economical benefit if this success rate could be improved. In view of the personal and societal burden of assisted pregnancy treatments, it is desirable to identify couples with a very low chance for success and couples with a high chance for spontaneous pregnancy, especially in couples where the cause of infertility is unknown and show a high rate of spontaneous pregnancy where expectant management could be desirable for them (M. Brandes et al., 2011, *Hum. Reprod* 26:360-368). Thus, both for improving the treatments and for deciding in individual cases whether to proceed, there is a need for models that can accurately predict if a woman will become pregnant and give live birth after IVF/ICSI. For over a decade, models have been available that predict the chance of live birth on the basis of clinical data including age, number of previous failed IVF attempts and probable reason for infertility (W. Templeton et al., 1996, *Lancet* 348:1402-1406). For large groups, the ratio of predicted versus observed live birth was 40%-60% (S. M. Nelson and D. A. Lawlor, 2011, *PLOS Medicine* 8:1-10). These authors developed an improved model on the basis of data from over 140,000 women, using more stratification on age and cause of infertility, the procedure (to be) used, source of the egg and duration of the child-wish. When the area under the curve for the reporter-operated curve (AU-ROC) of the new model is used for how well this new model functions, a slight but significant increase was reported (from 0.6184 to 0.6335). This model seems to give a good prediction on larger groups of women (more than 10,000). However, it is not known yet how well this model predicts on an individual basis.

The route to a live birth can be reduced to three critical steps: fertilization of the egg, acceptance of the fertilized egg by the female environment, and further development up to actual live birth. When the first step is artificially taken care of (like in IVF and ICSI), the chance to reach a live birth can be described by markers for the second step. However, the factors that are responsible for acceptance of the fertilized egg are virtually unknown. It is thus currently impossible to establish criteria that would predict success in this second step.

Therefore, there is still need for a model that can more reliably predict the chance of a successful IVF/ICSI treatment on an individual basis.

BRIEF SUMMARY

Disclosed herein is a model that can be developed that increases the predictability of the chance of a successful (or unsuccessful) IVF/ICSI treatment on an individual basis to 75%-100%.

The disclosure comprises a method for predicting the chance of a successful pregnancy in a subject comprising the steps of:
a. taking a urine sample;
b. determining the amount of the bacteria species *Lactobacillus* and *Staphylococcus* as a percentage of the total amount of bacteria present in the sample; and
c. predicting the chance of a successful pregnancy on the basis of the ratio between the bacteria.

Preferably, in the method disclosed herein, the subject is undergoing or eligible for an artificial insemination method, such as IVF or ICSI. In another preferred embodiment, the *Lactobacillus* species is *Lactobacillus crispatus* and the *Staphylococcus* species is *Staphylococcus aureus*.

Further preferred, the measurement of the amount of the bacteria is performed by PCR, more preferably qPCR, in which method *Staphylococcus* is preferably determined by using the primers 5'-GAGTAACACGTGGATAACCTAC-CTATAAGAC-3' (SEQ ID NO: 1) and 5'-GCATCGTTGC-CTTGGTAAGC-3' (SEQ ID NO: 2) and *Lactobacillus* is preferably determined by using the primers 5'-GATTTACT-TCGGTAATGACGTTAGGA-3' (SEQ ID NO: 3) and 5'-AGCTGATCATGCGATCTGCTTTC-3' (SEQ ID NO: 4).

Alternatively, the measurement of the amount of the bacteria is performed by mass spectrometry, more preferably MALDI-TOF mass spectrometry.

More specifically in the method according to the disclosure, the chance of a successful pregnancy is determined by the formula:

$$Y = a*(\% \ Lactobacillus) - b*(\% \ Staphylococcus) - c$$

wherein
a has a value from 0.025 to 0.051;
b has a value from 0.04 to 0.07;
c has a value from −1.10 to −0.66;
% *Lactobacillus* is the amount of *Lactobacillus* bacteria expressed as percentage of the total amount of bacteria;
% *Staphylococcus* is the amount of *Staphylococcus* bacteria expressed as percentage of the total amount of bacteria; and wherein Y represents the chance of success.

Preferably, in this formula, a has a value from 0.025 to 0.04, also preferably, b has a value from 0.04 to 0.06, and further, preferably, c has a value from −1.06 to −0.9, more preferably from −1.06 to −1.01.

The samples in which the bacteria are detected can be urinary samples, and preferably, the bacteria are detected in a mid-stream urine sample. The samples can also be vaginal samples, such as a vaginal smear.

The disclosure also comprises a kit for the prediction of the chance of a successful pregnancy, comprising:
  a. means for measuring the total content of bacteria in a sample from a subject;
  b. means for measuring the content of *Lactobacillus* bacteria;
  c. means for measuring the content of *Staphylococcus* bacteria; and
  d. means for calculating the chance according to the formula defined above.

Preferably, in such a kit, the means for measuring the content of *Lactobacillus* bacteria comprise the primers 5'-GATTTACTTCGGTAATGACGTTAGGA-3' (SEQ ID NO: 3) and 5'-AGCTGATCATGCGATCTGCTTTC-3' (SEQ ID NO: 4), while the means for measuring the content of *Staphylococcus* bacteria comprise the primers 5'-GAGTAACACGTGGATAACCTACCTATAAGAC-3' (SEQ ID NO: 1) and 5'-GCATCGTTGCCTTGGTAAGC-3' (SEQ ID NO: 2). Also preferred in such a kit is the means for measuring the total content of bacteria in a sample from a subject comprising a general primer set specific for bacterial 16s rDNA. More preferably, the general primer set comprises at least one forward and at least one reverse EUB primer.

Further preferred in the kit is the means for calculating the chance comprising a processor that is able to receive the measured bacterial values as input and that calculates the chance according to the formula as defined above. Preferably, the processor is able to output the chance to a signaling means, which can be read out by the person using the kit.

DETAILED DESCRIPTION

In the following description and examples, a number of terms are used. In order to provide a clear and consistent understanding of the specification and claims, including the scope to be given to such terms, the following definitions are provided. Unless otherwise defined herein, all technical and scientific terms used herein have the same meaning as commonly understood by one of ordinary skill in the art to which this disclosure belongs.

"IVF" or in vitro fertilization is a procedure in which eggs (ova) from a woman's ovary are removed. They are fertilized with sperm in a laboratory procedure, and then the fertilized egg (embryo) is returned to the woman's uterus.

"ICSI" stands for intracytoplasmic sperm injection, a test-tube fertilization procedure in which a sperm is injected directly into an egg to achieve fertilization. ICSI is done mainly for male infertility and can form part of an IVF procedure.

"Mid-stream urine" is defined herein as a urine specimen collected during the middle of a flow of urine, after the urinary opening has been carefully cleaned (by the urine that has flowed past). A mid-stream urine sample is also called a "clean catch specimen."

A "urinary tract infection" (UTI) is a bacterial infection that affects any part of the urinary tract. Symptoms include frequently feeling the need and/or the need to urinate, pain during urination, and cloudy urine.

"16S rDNA" is the DNA in the nucleoli of cell nuclei coding for a type of RNA subsequently forming the component of ribosomes on which the translation of messenger RNA into protein chains is accomplished. Comparison of gene sequences of the ribosomal RNA of different organisms has been used to determine evolutionary relationships among the organisms.

It has now been found that one of the factors that predicts the success of the settlement of the fertilized egg in the uterus is formed by the constitution of the bacterial population in the uro-genital area of the female. It is known that the composition of bacterial populations (like in the intestine or in the vagina) are a reflection of their direct environment and that this composition can change upon changes in that environment. This is, for instance, apparent in the finding that across all human population groups, the resident bacteria in the gut are not a random collection of the variety of bacterial species that we encounter. They are distinct populations that are in dynamic equilibrium with the environment provided by their host (M. J. Blaser and S. Falkow, 2009, *Nature Rev. Microbiol.* 7:887-894). The human intestines harbor bacteria that are accepted as they confer capacities that the human intestinal cells lack and that respond to the diet of their host (C. De Filippo et al., 2010, *PNAS* 107: 14691-14696). A change in diet is, in fact, a change in the chemical composition of the environment in which the bacteria live. Other environmental factors that will influence the composition of the gut microbiota include host factors like immune defense systems, cell surface characteristics and the physical characteristics of the niche where they reside (F. Backhed et al., 2005, *Science* 307:1915-1920).

An example from the uro-genital tract is the change in vaginal bacterial population that occurs when vaginal conditions change. Normally, the vagina provides a low pH environment that favors a population composed of 1 to 6 bacterial species and dominated by *Lactobacillus* species (D. N. Fredricks et al., 2005, *New Eng. J. Med* 353:1899-1911). The *Lactobacilli* further maintain the low pH and, in addition, actively defend their niche against other bacteria. In women with bacterial vaginosis, the pH is higher, the vaginal bacterial population is expanded to up to 17 species and the presence of *Lactobacilli* is greatly reduced in favor of pathogenic bacteria. The start of this shift in bacterial population composition may be either a decrease in *Lactobacillus* species or an invasion of other bacteria. The continuation, however, will be a shifting balance between a decrease in *Lactobacillus* species, increase in pH and increase in species like *Staphylococcus* that thrive in the new situation. It remains to be established if these shifts precede symptoms of vaginosis.

Indication that bacterial populations may be used to predict specific situations was found in a small study on men with and without urethritis where bacterial populations were investigated with broad-spectrum 16s rDNA analysis (W. A. Riemersma et al., 2003, *J. Clin. Microbiol.* 41:1977-1986). The presence of three hitherto unknown bacteria was associated with absence of urethritis.

In the investigation that generated this disclosure, basically, two questions were asked: does the urine bacterial population in a woman hold information as to whether the internal environment of that woman is suitable for IVF or ICSI to achieve pregnancy and is the bacterial population related to a changed risk for urinary tract infection? The idea behind the first goal is that the first step to success of IVF or ICSI is acceptance of a foreign body, the fertilized egg, by the internal environment of the woman during the period that the egg must nest. This internal environment will be under hormonal regulation. The nature of this regulation is not fully known but it is likely that it will not only affect the conditions in the uterus but also conditions elsewhere in the body like the urinary tract. Thereby it will affect the acceptance of foreign bodies, the resident bacterial population, in that urinary tract. Based on this idea, two hypotheses were formulated that drove the investigation: first, that bacterial populations in women indicate how well a fertilized egg will be accepted and, second, that bacterial populations in the urine will react to the environmental changes that occur in a woman when she becomes pregnant. During pregnancy, the urinary tract undergoes anatomic changes like dilation of the renal pelvis and urethra, displacement of the bladder and urinary stasis related to relaxation of bladder smooth muscle, and chemical changes (urine pH, urine osmolality, glycosuria and aminoaciduria). These changed conditions can be expected to be more hospitable to bacterial types other than the resident bacteria. Since resident bacteria can also be the source of problems inside the urinary tract itself (infection), the relation between bacterial population composition in the urine and urinary tract infection was also investigated in this study.

In this study, it appeared that a core group of five bacterial species/strains was found under all circumstances tested (pregnant, not pregnant, not pregnant after IVF/ICSI). *Lactobacillus crispatus* and *Staphylococcus aureus* were present in the majority of all samples, while *E. coli, Streptomyces* sp. and uncultured bacterium isolate CH96Fc_H10 were found in a smaller number of samples. In all women, more than 70% of the total population consisted of maximal four types that individually were present in more than 10% of the total population. This included the five mentioned bacterial species plus a shortlist of other types (see Table 5). A long list of bacterial types was found in small percentages in one or a few number of samples (see Table 3).

The core group of five bacterial species that was found in women under all of the test conditions may represent species that have a high chance of invading the urinary tract from an outside pool, that adapt better to the conditions in the urinary tract or that are better accepted by the host. The second group consists of species that are found infrequently, but that can persist over time in individual women and even become the dominant species. Reasons why these species are not found more often may be that exposure of the urinary tract to outside pools for these bacteria is not the same for all women or that specific host factors allow their presence only in a small subset of women. The large number of species that was found only in one single sample may represent passers-by that do not survive well in the urinary tract.

What can be concluded from the study is that when a women becomes pregnant, the composition of the bacterial population in the urinary tract changes dramatically. Before pregnancy, the bacterial population is dominated by various *Lactobacillus* strains (mainly *L. crispatus*). During pregnancy, *Lactobacillus* is replaced by other bacteria, mainly *Staphylococcus aureus*, that often become the dominant species. This shift was not due to the procedure that the women underwent since it did not occur in women who underwent IVF/ICSI but did not get pregnant.

Of course, the finding that the urinary tract population reflects if a woman is pregnant is clinically irrelevant, since there are easier ways to determine pregnancy. The relevancy is given by the observation that apparently the fertility state of the woman influences the bacterial population in the urinary tract. This supports the hypothesis that the bacterial population in the urinary tract is a marker for the internal conditions of the host.

The study shows that this marker function is sufficiently specific for diagnosing the fertility of a woman who wants to become pregnant. As is clear from the experimental section, a model built on the relative presence of *Lactobacillus* species and *Staphylococcus* species in the urine before the IVF/ICSI procedure can predict if IVF/ICSI will be successful or not.

Accordingly, the disclosure provides for a method for predicting the chance of a successful pregnancy in a subject comprising the steps of:
  a. taking a urine sample;
  b. determining the amount of the bacteria species *Lactobacillus* and *Staphylococcus* as a percentage of the total amount of bacteria present in the sample; and
  c. predicting the chance of a successful pregnancy on the basis of the ratio between the bacteria.

Such a method, although preferred for subjects that are undergoing or eligible for an artificial insemination method, like IVF or ICSI, is not limited to such an extent. The method can also be useful for subjects who are interested what their chances to become pregnant in a natural way would be. In this respect, it is remarkable that when samples are taken from male subjects, from young females or from women who already are pregnant, i.e., subjects that cannot become pregnant, the method also is able to give a correct prediction: from these samples, it appeared that the outcome of the test was negative. Of course, in cases where no artificial insemination is used, the chance of a successful pregnancy calculated as above is only related to those situations in which the chance to become pregnant is not influenced by infertility of the partner or by gross physiological malfunction in the female subject (e.g., the absence of a uterus, hormonal imbalance, etc.).

Preferably, the *Lactobacillus* species to be detected is *Lactobacillus crispatus*. However, it may be useful to also detect other *Lactobacillus* species, such as *L. jensenii, L. iners* and *L. gasseri*. These species were encountered in some of the women and inclusion of these species into the group of Lactobacillae increases the predictive power of the above method. The same is true for *Staphylococcus* where, not only *Staphylococcus aureus*, but also *S. epidermidis, S. haemolyticus* and *S. cohnii* were encountered and found to add to the predictive power. Preferably, the detection of the bacterial species in the method of the disclosure takes place through molecular biological assays, such as PCR and preferably qPCR. In such an assay, the bacteria are detected and quantified by amplification with primers that are specific for the bacteria to be detected. In the case of *Lactobacillus*, this means that primers specific for *L. crispatus* may be used, but that preferably such primers also would recognize other *Lactobacillus* species, as mentioned above. Currently, an optimal detection method comprises the *Lactobacillus*-specific primers as used in Example 2.

A similar method of operating also applies to the detection of *Staphylococcus* species, where predominantly *S. aureus* should be detected, but also where detection of *S. epidermidis, S. haemolyticus* and *S. cohnii* may be encompassed. Also, in this case, the primer set as shown in Example 2 gives optimal results.

It should, however, be understood that it is not the absolute ratio of the detected *Lactobacillus* and *Staphylococcus* that should be used. Rather, the ratio of the percentages of these bacteria with regard to the total content of bacteria is used. In order to determine the total content of bacteria in the sample, it is preferred to use primers that recognize the bacterial 16s rDNA which opens the opportunity to use primers that recognize conserved parts of the 16S rDNA that are present in all bacteria. Primer sets that are specific for the bacterial 16s rDNA and, therefore, able to recognize only bacteria in a sample in which biological material from other organisms is present, have been described in the literature. In Wikipedia (http://en.wikipedia.org/wiki/16S_ribosomal_RNA), the following primers are described:

Table

| Primer name | Sequence (5'-3') |
|---|---|
| B27F | AGA GTT TGA TCC TGG CTC AG (SEQ ID NO: 5) |
| U1492R | GGT TAC CTT GTT ACG ACT T (SEQ ID NO: 6) |
| 928F | TAA AAC TYA AAK GAA TTG ACG GG (SEQ ID NO: 7) |
| 336R | ACT GCT GCS YCC CGT AGG AGT CT (SEQ ID NO: 8) |
| 1100F | YAA CGA GCG CAA CCC (SEQ ID NO: 9) |
| 1100R | GGG TTG CGC TCG TTG (SEQ ID NO: 10) |
| 337F | GAC TCC TAC GGG AGG CWG CAG (SEQ ID NO: 11) |
| 907R | CCG TCA ATT CCT TTR AGT TT (SEQ ID NO: 12) |
| 785F | GGA TTA GAT ACC CTG GTA (SEQ ID NO: 13) |
| 805R | GAC TAC CAG GGT ATC TAA TC (SEQ ID NO: 14) |
| 533F | GTG CCA GCM GCC GCG GTA A (SEQ ID NO: 15) |
| 518R | GTA TTA CCG CGG CTG CTG G (SEQ ID NO: 16) |

A very well-suited primer set uses so-called EUB primers, of which several are available (e.g., EUB fy33 and EUB r1387; EUB 8f and EUB 536r, EUB 341 and EUB 534, etc.). Also, kits for detecting bacterial 16s rDNA on the basis of EUR primers are commercially available (such as the ONAR®EUB kit from Iris Technologies Int., Cursdorf, Germany).

In another embodiment of the disclosure, the amounts of bacteria in the sample are determined by spectrographical means, such as mass spectrography, Raman spectrography, and the like. Preferably, in such a measurement of the amount, MALDI-TOF is used as the analytical tool.

When the amounts of total bacteria and the amounts of *Lactobacillus* and *Staphylococcus* are determined, in a preferred embodiment of the disclosure, the ratio of the bacteria, and thus the chance of a successful pregnancy, can be calculated according to the formula:

$$Y = a*(\% \text{ Lactobacillus}) - b*(\% \text{ Staphylococcus}) - c$$

wherein
a has a value from 0.025 to 0.051;
b has a value from 0.04 to 0.07;
c has a value from −1.10 to −0.66;
% *Lactobacillus* is the amount of *Lactobacillus* bacteria expressed as percentage of the total amount of bacteria;
% *Staphylococcus* is the amount of *Staphylococcus* bacteria expressed as percentage of the total amount of bacteria; and
wherein Y represents the chance of success.

The value of Y may be converted to a chance that ranges between 0 (no chance of success) and 1 (certain success) by the formula:

$$\text{Chance} = e^Y/(1+e^Y)$$

Depending on the constants that are used, the value of Y will vary between 4.44 (100% *Lactobacillus*, a=0.051 and c=−0.66) to −8.1 (100% *Staphylococcus*, b=0.07 and c=−1.1). For the comparison of predicted pregnancy versus actual pregnancy, the best cut-off value was found to be chance=0.5. A value Y equal to or higher than 0.5 then predicts success and a value lower than 0.5 predicts failure. With this cut-off value, the formula correctly predicted pregnancy after the first attempt of IVF/ICSI in 86% of the women and correctly predicted pregnancy after multiple attempts during 1 year in 92.3% of the women. Thus, in 7.7% of cases, the formula predicted failure while the women did become pregnant after IVF/ICSI (false negative). In 3.8%, the pregnancy was not completed due to a miscarriage. In 3.8%, the formula missed the actual live birth. In 25% of the cases where the formula predicted pregnancy, no ongoing pregnancy was achieved (false positive).

Since women who want to become pregnant and use a predictive test to decide whether or not to proceed with IVF/ICSI will especially not accept a false negative prediction, it is desirable to reduce the false-negative predictions from 3.8% to zero. In that case, the cut-off value must be lowered to 0.04. However, at this cut-off value, the formula predicts pregnancy for all women, which, of course, is also not desired.

For the best prediction of completed pregnancy, a formula is used where a has a value from 0.03 to 0.051, while, further preferably, b has a value from 0.056 to 0.064. Further preferred, c has a value from −1.06 to −1.03. The cut-off for the chance to obtain pregnancy then, preferably, is 0.5.

A sample from a subject is preferably a urine sample, more preferably, a mid-stream urine sample. Such a mid-stream urine sample is preferred, since this best represents the bacterial population in the urine. This is because the first urine is rinsing the urethra and would take along bacteria that populate the urethra.

It is also possible to perform the method of the disclosure on a vaginal sample. Since the same types of bacteria are encountered in the vagina, it is plausible that a similar ratio and, preferably, a similar formula for predicting the chance on a successful pregnancy can be used as for urinary samples. It is possible that the values of a, b and c need to be optimized, but such optimization is well within the skill of the artisan.

Also part of the disclosure is a kit for determining the chance of a successful pregnancy. Such a kit would comprise means for determining the total content of bacteria in the sample and means for detecting both the *Lactobacillus* and *Staphylococcus* bacteria. Further, such a kit would comprise means for calculating the chance on the basis of the formula as represented above.

Such means for calculating the chance would preferably comprise a processor that is able to receive the values of the detection of the total content of bacteria and the specific above-mentioned genera/species of bacteria. The processor then will calculate Y according to the formula of the disclosure and will output the chance of a successful pregnancy. This output can be in the form of a numerical value (the actual value of Y resulting from the formula), but it can also be an indication of the chance, e.g., through a signaling light source, which will either be red (negative) or green (positive) chance, or through a color-coded bar, representing the numerical value of Y, where the negative values show a gradient from dark red (strongly negative) via light red (medium negative) to yellow (about zero) and the positive values show a gradient from yellow (about zero) via light green (medium positive) to dark green (strongly positive). In such a way, the subject can receive a visual indication of the reliability of the prediction. In all applications, an option can be included where the cut-off value for the chance, which is standard set at 0.5, is lowered to reduce the number of false negative predictions at the cost of increasing the number of false positive predictions. Of course, other indications representing the value of Y would be possible, and the skilled person will be able to design variants on the above embodiments without departing from the gist of the disclosure.

EXAMPLES

Patient Inclusion and Group Assignment

In 2005 and 2006, 98 women who visited the IVF ward of the ErasmusMC in Rotterdam were enrolled in the study. Of these 98 women, 40 (41%) became pregnant during the three-year study after, in some cases, multiple attempts. After giving informed consent and instruction on how to perform a mid-stream urine collection, the women delivered a mid-stream urine sample during the first visit and answered questions on previous use of antibiotics and previous UTI. They received a urine container and a folder describing the procedure of mid-stream urine collection. The women were reminded to collect the second sample when they were either in their $16^h$ week of pregnancy or at a comparable time after placement of the embryo for those women who had not become pregnant. The urine sample was returned to the hospital the same day or frozen and returned at a later date. After collection of the second sample, the women were followed for a maximum of three years to collect data on the outcome of the pregnancy and on later pregnancies.

Of the 98 women, 16 did not answer all questions on the questionnaire or did not return an intact second urine sample. These were excluded from our discovery study that requires samples at two time points. From the remaining 82 women, the first 21 who became pregnant by the first IVF/ICSI cycle that followed the first urine sample were included for the discovery study. Twenty-one women who were not pregnant when they collected their second sample (16 weeks after placement of the embryo) were included into the group of non-pregnant women. After the inclusion round, it was found that one of the 21 non-pregnant women was pregnant when she collected her second sample. She was reassigned to the pregnant group. This resulted in a pregnant group of n=22 and a not pregnant group of n=20. In these 42 women, the bacterial population was determined in both urine samples by broad spectrum 16S rDNA analysis. Furthermore, the women were clinically followed for three years with respect to pregnancies and outcomes thereof. The bacterial species identified in the first urine sample of all 42 women were used to build a model that predicts the outcome of IVF/ICSI (pregnant/not pregnant). The changes in bacterial population that occurred when women became pregnant were compared to changes in the main causes of UTI. The latter was obtained from a separate group (see below).

From the remaining 40 women who returned both urine samples and a complete questionnaire, plus women who did return both an intact first sample and a complete questionnaire, an independent validation group, n=42, was formed. In this group, the predictive model obtained above was validated using a qPCR test that was based on primers specific to the bacteria that are included in the predictive model.

Note that due to the selection protocol, the pregnancy success rate in the discovery phase was 22/42=52%, compared to the 41% for the whole group of 98 women.

The characteristics of the groups are shown in Table 1.
Exclusion Criteria

Women who used antibiotics or had a UTI during the 16-week study period were excluded.
Follow-Up Data (3-Year Period)

In four women of the pregnant group, the pregnancy ended in miscarriage (3) or intra uterine death (IUD). After additional procedures, all four had successful pregnancies within 6 months after the second sample was collected.

Of the failed IVF group, twelve women never became pregnant, seven were not pregnant during collection of the second sample but were pregnant at another time point. These were:

Patient 6, pregnant >1 year after first sample, <1 year after second sample

Patient 10, pregnant within 1 year after first sample (twin)

Patient 14, pregnant within 1 year after first sample

Patient 19, within 1 year after first sample, miscarriage

Patient 58 was found to be spontaneously pregnant around the time of collection of the first sample. This resulted in IUD. IVF followed, and 16 weeks after placement of the embryo, the second sample was collected. The IVF failed. This patient was assigned to the not-pregnant group for the test of outcome of the first IVF/ICSI and the test of changes due to pregnancy. For completeness, the model building was also performed with patient 58 being assigned to the pregnant group. She was assigned to the pregnant group for the test of whether a woman could become pregnant within 1 year.

Patient 78, spontaneously pregnant >1 year after first and second samples, miscarriage.

Patient 92, pregnant (IVF)>1 year after first and second samples, miscarriage, then successful spontaneous pregnancy 2 years after first sample.
Predictive Model for Success of IVF/ICSI The data of the bacterial population of the first urine sample was entered into binomial regression analysis to build two models. Model 1 predicts if the first IVF/ICSI attempt will achieve pregnancy. Model 2 predicts if a woman will become pregnant during 1 year of IVF/ICSI attempts (1 to 3 attempts). For this model, patients 10, 14 19 and 58 who became/were pregnant within 1 year after collection of the first urine sample, on which the model is based, were reassigned to the pregnant group, yielding a pregnant group of n=26 and a not pregnant group of n=15. Patients 6, 78 and 92 stayed in the not pregnant within 1 year group because their pregnancy started more than 1 year after collection of the second sample. The predictive models were applied to the urine samples collected at week 16. The models based on broad range analysis were translated into a species-specific QPCR test that was validated in the independent test group.
Bacterial Population and Causes of UTI in Non Pregnant and Pregnant Women.

The bacterial populations found with DNA analysis represent bacteria that are present in low numbers in the urinary tract of pregnant/non pregnant women without UTI. This data was compared to data on causes of UTI and vaginal infection in pregnant/non pregnant women obtained by urine and vaginal smear cultures from women attending the Maternity Hospital in Erbil (Kurdistan Region, Iraq). During 2009, in total, 599 urine culture results (210 not pregnant and 389 pregnant) and 216 vaginal smear culture results (94 not pregnant and 122 pregnant) were obtained.

TABLE 1

Characteristics two patient groups

|  |  | Pregnant | Not pregnant |
|---|---|---|---|
| Age |  | 32.7 ± 3.7 | 33.6 ± 5.9 |
| BMI |  | 25.0 ± 4.1 | 22.9 ± 2.7 |
| Smoking |  | 1 | 1 |
| Duration child-wish in years |  | 4.1 ± 3.4 | 6.0 ± 5.4 |
| Cause | Male | 10 | 7 |
|  | Male/pesa | 1 | 1 |
|  | Male/tuba |  | 1 |
|  | Cervix |  | 1 |
|  | cycle problems | 3 | 1 |
|  | Unknown | 5 | 7 |
|  | Endometriosis |  | 1 |
|  | after ovarectomy | 1 |  |
|  | Pof | 1 |  |
|  | Tuba | 1 | 1 |

Methods

DNA Purification.

Bacterial population composition was assessed by broad spectrum bacterial 16S rDNA analysis (W. A. Riemersma et al., 2003, *J. Clin. Microbiol.* 41:1977-1986). Urine samples were centrifuged at 800 g for 10 minutes. The pellet was stored at −80° C. until further use. Then, 150 µl of the pellet was used for DNA extraction and purification. To samples with a volume of <150 µl, a compensating amount of 50 mM Tris-HCl (pH 7.5) −0.1 mM EDTA-50 mM glucose buffer was added. First, 75 µl of lysostaphin solution (10 mg/ml; Sigma, St. Louis, Mo.) was added, and the mixture was heated to 37° C. for 30 minutes. Thereafter, 1 ml of guanidinium lysis buffer (4 mM guanidinium isothiocyanate, 0.1 M Tris-HCl [pH 6.4], 0.2 M EDTA, 0.1% TRITON® X-100) was added, and the mixture was kept at room temperature for 1 hour, after which 50 µl of Celite suspension was added. The samples were mixed at regular intervals for 10 minutes at room temperature. After vortexing and centrifugation (10 minutes at 14,000 rpm in an Eppendorf centrifuge), the supernatant was discarded and the pellet was washed twice with a second lysis buffer (4 M guanidinium isothiocyanate, 0.1 M Tris-HCl; pH 6.4), twice with ethanol (70%) and finally once with acetone. The pellet was vacuum dried and emulsified in 100 µl of 10 mM Tris-HCl (pH 8.0). The sample was heated to 56° C. for 10 minutes and centrifuged (10 minutes at 14,000 rpm in an Eppendorf centrifuge). The supernatant was used as a template for PCR in a buffer (pH 7.5) containing 50 mM Tris-HCl, 0.1 mM EDTA and 50 mM glucose.

PCR

Isolation of bacterial 16S rDNA from the purified DNA was performed with a PCR reaction using primers directed against the conserved part of the gene, EUB-L (5'-CTT-TACGCCCATTTAATCCG-3' (SEQ ID NO: 17)) and EUB-R (5'-AGA-GTTTGATCCTGGTTCAG-3' (SEQ ID NO: 18)). The PCR generates an ~500-bp fragment deriving from the 3'-terminal end of the small-subunit (ssu) rRNA gene (K. H. Wilson et al., 1990, *J. Clin. Microbiol.* 28:1942-1946). To 5 µl of the purified DNA solution, 45 µl of PCR mix was added (10 µl 20 mM desoxynucleotide triphosphate stock solution (Amersham Life Science, Cleveland, Ohio), 5 µl 10-fold-concentrated SuperTaq PCR buffer (HT Biotechnology, Cambridge, United Kingdom), 0.5 µl of both primers, 28.92 µl distilled water, and 0.08 µl SuperTaq polymerase (15 U/µl; HT Biotechnology, Cambridge, United Kingdom). The PCR reaction included a precycling denaturation step at 94° C. for 5 minutes followed by 30 cycles of denaturation at 94° C. (45 seconds), annealing at 55° C. (45 seconds), and extension at 72° C. (45 seconds). As control sample, 50 µl of PCR mix without additional DNA samples was run in parallel. Then, 10-µl portions of the PCR products were analyzed on a 1% agarose gel containing ethidium bromide. Electrophoresis was performed in 0.5× TBE (50 mM Tris, 50 mM borate, 1 mM EDTA); gels were stained in aqueous ethidium bromide (10 ng/ml) and photographed under UV illumination.

Cloning of Amplification Products.

The PCR amplification products contain a mix of 16S rDNA fragments that originate from the different bacteria that were present in the urine. To separate these fragments, a cloning-transformation step was done. Of each PCR product, 3 µl was used for ligation in a pGEM-T easy vector and transformed by heat-shock into competent *Escherichia coli* JM109 cells. Clones were grown overnight at 37° C. on LB agar plates containing ampicillin (100 µg/ml) and X-Gal (5-bromo-4-chloro-3-indolyl-β-D-galactopyranoside; 40 µg/ml). Transformants were identified by blue-white colony screening.

Sequencing.

Of all clones that contained the plasmid with insert, the plasmids were isolated using a QIAGEN® MINIPREP™ kit (QIAgen, Venlo, The Netherlands). A maximum of 100 clones were used per sample. For each plasmid isolate, a sequencing PCR was performed with the T7 primer directed at the variable portion of the 16S rDNA, TAATACGACT-CACTATAGGG (SEQ ID NO: 19). The resulting sequence was used to identify the original bacterial type in the BLAST database. All outcomes were related to the total number of clones that was analyzed to obtain the percentage of the population that is represented by a specific bacterial type. Thus, when 100 clones were analyzed and 20 yielded the sequence for *Lactobacillus crispatus,* 20% of the population was *Lactobacillus crispatus.*

The PCR approach yields a qualitative analysis of the bacterial population in the original urine sample. Cultures yielding quantitative data were not performed in these women without symptoms of infection.

Statistics.

All statistical tests were performed with the PASW 17.0 program (SPSS). Differences between the first and second samples within groups were tested for significance with a paired Student t-test. Differences between groups were tested with an unpaired Student t-test with equal variance of the two groups.

Predictive models were obtained by binomial regression analysis.

Results

Composition and Stability of the Bacterial Population

All urine samples had bacterial populations that consisted of 1 to 10 bacterial types. Table 2 shows the results for two women, one who got pregnant and one who did not get pregnant. Apart from the various types of bacteria that are found, it is also of interest to determine how stable these bacterial populations are over time in women who become pregnant or not. A first measure of stability is to look qualitatively at the number of bacterial types from the first sample that is found back in the second sample. In Table 2, theses are depicted in bold numbers. Thus for the pregnant woman, three out of four bacterial types (75%) remained present over a time period of >16 weeks (*Lactobacillus crispatus* strain ZDY35b, *Staphylococcus aureus* strain LA14 and *Pseudomonas acephalitica,* 75% overlap). In the woman who did not become pregnant, the overlap was 60%.

A second measure for stability is the absolute overlap in percentages between the two samples. For the pregnant woman, 37% of the population was identical for both time points (12% *Lactobacillus crispatus,* 15% *Staphylococcus aureus,* 10% *Pseudomonas acephalitica*). A large shift occurred from *Lactobacillus crispatus* to *Staphylococcus aureus*. In the woman who did not become pregnant, 79% of the population was identical before versus after IVF.

TABLE 2

|  | Pregnant | | Not pregnant | |
| --- | --- | --- | --- | --- |
|  | 1$^{st}$ sample | 2$^{nd}$ sample | 1$^{st}$ sample | 2$^{nd}$ sample |
| *Lactobacillus crispatus* strain ZDY35b | 50% | 12% | 27% | 20% |
| *Staphylococcus aureus* strain LA14 | 15% | 78% | 53% | 60% |
| *Pseudomonas acephalitica* | 30% | 10% |  |  |
| *Streptomyces* sp. SD-Z | 5% | 0% |  |  |
| *Brevundimonas* sp. DB5 |  |  | 14% | 0% |

TABLE 2-continued

|  | Pregnant | | Not pregnant | |
| --- | --- | --- | --- | --- |
|  | 1$^{st}$ sample | 2$^{nd}$ sample | 1$^{st}$ sample | 2$^{nd}$ sample |
| Uncultured bacterium clone Toolik_Jun2005_Intertussock_69 |  |  | 6% | 15% |
| *Streptomyces* sp. WYE2 |  |  | 0% | 5% |

Applying this analysis to the whole groups shows that:

For the pregnant group, the average number of bacterial species was 4 in both samples. For the not pregnant group, this number was 3 before and 4 after the IVF/ICSI attempt. In the pregnant group, on average 1.9±1.2 bacterial types were present in both samples. For the not pregnant group, the number was 2.1±0.9. The variety of species did not differ significantly between both groups.

The exact overlap between the first and second sample was significantly lower ($p<0.001$) in the pregnant group, 37±23%, as compared to the not pregnant group, 68±24%.

Overall, the bacterial population was stable, both qualitatively and quantitatively, in women who did not become pregnant. In women who did become pregnant, large shifts occurred within the existing population in the abundance of individual bacterial types. The nature of this shift is given below.

TABLE 3a

Bacteria identified by broad range 16S rDNA PCR (match >97%) in urine of women before a successful IVF/ICSI procedure. Matching <97% is shown as (value).

| Patient number | 1 | 3 | 5 | 8 | 9 | 11 | 17 | 18 | 20 | 22 | 32 | 33 | 34 | 35 | 38 | 39 | 50 | 61 | 63 | 67 | 69 | 87 | % women |
|---|---|---|---|---|---|---|---|---|---|---|---|---|---|---|---|---|---|---|---|---|---|---|---|
| number of clones analysed | 100 | 100 | 100 | 100 | 100 | 100 | 100 | 100 | 100 | 100 | 60 | 60 | 60 | 60 | 60 | 100 | 100 | 60 | 100 | 60 | 100 | 100 | percentage of population |
| Lactobacillus, all species | 58 | 100 | 70 | 58 | 25 | 48 | 86 | | 66 | 86 | 82 | 52 | 64 | 50 | 75 | 50 | 71 | 70 | 61 | 52 | 57 | 79 | 95 |
| Lactobacillus crispatus (89% match) | 58 | 100 | | 58 | 25 | | 86 | | 66 | | | | | | | | | | 61 | | 57 | | 36 |
| Lactobacillus crispatus strain AG1 | | | 70 | | | | | | | | | | | | | | | | | | | | 5 |
| Lactobacillus crispatus clone B225 | | | | | | 48 | | | | | | | | | | | | | | | | | 5 |
| Lactobacillus crispatus strain BJ H33h | | | | | | | | | | | | | | | 75 | | | | | | | | 5 |
| Lactobacillus crispatus clone FX12-5 | | | | | | | | | | | | | | | | 50 | | | | | | | 5 |
| Lactobacillus crispatus clone FX32-3 | | | | | | | | | | | 82 | | | | | | | | | | | | 5 |
| Lactobacillus crispatus clone FX36-3 | | | | | | | | | | | | 52 | | | | | | | | 52 | | | 5 |
| Lactobacillus crispatus strain LAB32 | | | | | | | | | | | | | | | | | | 70 | | | | | 5 |
| Lactobacillus crispatus strain TL13 | | | | | | | | | | | | | | | | | 71 | | | | | | 5 |
| Lactobacillus crispatus strain ZDY35b | | | | | | | | | | | | | 64 | 50 | | | | | | | | 79 | 14 |
| Lactobacillus jensenii C72 | 6 | | | | 45 | | | | | | | | | | | | | | | | | | 9 |
| Staphylococcus, all species | | | | | | | | | | 86 | 6 | 16 | 12 | 15 | 25 | | | | | 12 | | 6 | 45 |
| Staphylococcus aureus | 6 | | | | | | | | | | 6 | 16 | 12 | | 25 | | | | | 12 | | | 18 |
| Staphylococcus aureus FD42 | 6 | | | | | | | | | | | | | | | | | | | | | | 5 |
| Staphylococcus aureus strain iZBN11 | | | | | | | | | | | | | | | | | | | | | | | 0 |
| Staphylococcus aureus strain I65 | | | | | | | | | | | | | | | 15 | | | | | | | | 5 |
| Staphylococcus aureus strain LA14 | | | | | | | | | | | | | | | | | | | | | | | 0 |
| Staphylococcus aureus clone MT10B_A04 | | | | | | | | | | | | | | | 25 | | | | | | | | 5 |
| Staphylococcus aureus strain YT-2 | | | | | | | | | | | | | | | | | | | | | | | 0 |
| Staphylococcus haemolyticus strain N11 | | | | | | | | | | | | | | | | | | | | | | | 9 |
| Staphylococcus epidermidis | | | | | | | | | | | | | | | | | | | | 4 | | 6 | 9 |
| Bacillus, all species | | | | | 45 | | 2 | 51 | 22 | 14 | | 4 | | | | 50 | 10 | | 9 | 4 | 23 | | 50 |
| Bacillus sp. A12 | | | | | | | | | | | | | | | | | | | | | 23 | | 5 |
| Bacillus sp. BY143(A)Ydz-ds (96% match) | | | | | 30 | | 2 | | 22 | | | | | | | 50 | 10 | | 9 | 4 | | | 5 |
| Bacillus sp. CPB 8 | | | | | 30 | | | 51 | | | | | | | | | | | | | | | 5 |
| Bacillus sp. GNA22 | | | | | | | | | | | | | | | | | | | 9 | | | | 5 |
| Bacillus sp. HPC 1303 | | | | | | | 2 | | | 14 | | | | | | | | | | | | | 5 |
| Bacillus sp. RG1 | | | | | | | | | | | | | | | | 50 | | | | | | | 5 |
| Bacillus sp. RG4 | | | | | | | | | | | | | 8 | | | | | | | | | | 14 |
| Broad-Range 16S rDNA PCR clone | | | | | | | | | | | | | | | | | | | | | | | % women |
| Bacilli bacterium clone MS145A1_G04 | | | | | | | | | | | | | 4 | | | | | | | | | | 0 |
| Bacillus cereus | | | | | | | | | | | | | 4 | | | | | | | | | | 5 |
| Bacillus subtilis strain WXZ-5 | | | | | | | | | | | | | | | | | | | | | | | 5 |
| Escherichia, all species | 8 | | | 18 | 2 | | | | | | | | | | | | | | 10 | | 20 | | 27 |
| E. coli | 8 | | | 4 | 2 | | | | | | | | | | | | | | | | 20 | | 18 |
| Escherichia coli str. K12 | | | | | | | | | | | | | | | | | | | | | | | 0 |
| Escherichia fergusonii | | | | | 4 | | | | | | | | | | | | | | | | | | 5 |
| Escherichia sp. EMB 210 | | | | | 10 | | | | | | | | | | | | | | | | | | 5 |
| Corynebacterium, all species | 2 | | | | | | | | | | | | | | | | | | | | | 5 | 14 |
| Corynebacterium mastitidis | | | | | | | | | | | | | 8 | | | | | | | | | | 0 |

TABLE 3a-continued

Bacteria identified by broad range 16S rDNA PCR (match >97%) in urine of women before a succesfull IVF/ICSI procedure. Matching <97% is shown as (value).

| | Patient number | | | | | | | | | | | | | | | | | | | | | | |
|---|---|---|---|---|---|---|---|---|---|---|---|---|---|---|---|---|---|---|---|---|---|---|---|
| | 1 | 3 | 5 | 8 | 9 | 11 | 17 | 18 | 20 | 22 | 32 | 33 | 34 | 35 | 38 | 39 | 50 | 61 | 63 | 67 | 69 | 87 | |
| | number of clones analysed | | | | | | | | | | | | | | | | | | | | | | |
| | 100 | 100 | 100 | 100 | 100 | 100 | 100 | 100 | 100 | 100 | 60 | 60 | 60 | 60 | 60 | 100 | 100 | 60 | 100 | 60 | 100 | 100 | |
| Corynebacterium sp. clone T0079 | 2 | | | | | | | | | | | | | | | | | | | | | | 5 |
| Corynebacterium sp. R603 | 6 | | | | | | | | | | | | | | | | | | | | | | 0 |
| Corynebacterium tuscaniense strain ISS-5309 | 6 | | | | | | | | | | | | | | | | | | | | | | 5 |
| Corynebacterium xerosis | | | | | | | | | | | | | | | | | | | | | | 5 | 18 |
| Streptococcus, all species | | | | | | | | | | | | 16 | | | | | | 7 | | 4 | | | 5 |
| Streptococcus | | | | | | | | | | | | | | | | | | 7 | | | | | 0 |
| Streptococcus anginosus strain ChDC YA12 | | | | | | 24 | 8 | | | | | | | | | | | | | | | | 5 |
| Streptococcus anginosus clone UR062 | | | | | | | | | | | | 16 | | | | | | | | | | | 18 |
| Streptococcus anginosus strain VAMC5302 | | | | | | | | | | | | | | | | | | | | 4 | | | 5 |
| Streptococcus intermedius strain TG14 | | | | | | | 8 | | | | | | | | | | | | | | | | 5 |
| Streptomyces, all species | | | | | | | | | | | | | | 5 | | | | 5 | | 4 | | 5 | 18 |
| Streptomyces sp. SC-13 | | | | | | | | | | | | | | | 5 | | | | | | | | 5 |
| Streptomyces sp. SD-Z | | | | | | | | | | | | | | | 5 | | | | | | | | 9 |
| Streptomyces sp. SX-3 | | | | | | | | | | | | | | | | | | 5 | | 4 | | | 18 |
| Pseudomonas, all species | | | | | | 24 | | | | | | | 4 | 30 | | | | | | | | | 9 |
| Pseudomonas acephalitica | | | | | | | | | | | | | 4 | 30 | | | | | | | | | 0 |
| Pseudomonas fulva | | | | | | | | | | | | | | | | | | | | | | | 5 |
| Pseudomonas fluorescens | | | | | | 24 | | | | | | | | | | | | | | | | | 5 |
| Pseudomonas sp. 5S2.A12 | | | | | | | | | | | | | | | | | | | | | | | |

TABLE 3b

Bacteria identified by broad range 16S rDNA PCR (>97% match) in urine of women during pregnancy. Matching <97% is shown as (value).

| Bacteria | \multicolumn{22}{c}{Patient number} | % women |
|---|---|---|---|---|---|---|---|---|---|---|---|---|---|---|---|---|---|---|---|---|---|---|---|
| | 1 | 3 | 5 | 8 | 9 | 11 | 17 | 18 | 20 | 22 | 32 | 33 | 34 | 35 | 38 | 39 | 50 | 61 | 63 | 67 | 69 | 87 | |
| | \multicolumn{22}{c}{Number of clones analyzed} | percentage of population |
| | 100 | 100 | 100 | 100 | 100 | 100 | 100 | 100 | 100 | 100 | 60 | 60 | 60 | 60 | 60 | 100 | 100 | 60 | 100 | 60 | 100 | 100 | |
| *Lactobacillus*, all species | 10 | 50 | | 37 | 15 | 30 | 59 | | | | | | | | | 17 | | 28 | 23 | 22 | 16 | 25 | 73 |
| *Lactobacillus crispatus* | 10 | 50 | | 37 | 15 | 30 | 59 | | | | | | | | | | | | 23 | | 16 | | 32 |
| *Lactobacillus crispatus* strain AG1 | | | | | | | | | | | | | | | | | | | | | | | 5 |
| *Lactobacillus crispatus* clone B225 | | | | | | 30 | | | | | | | | | 24 | | | | | | | | 5 |
| *Lactobacillus crispatus* strain BJ H33h | | | | | | | | | | | | | | | | 17 | | | | | | | 0 |
| *Lactobacillus crispatus* clone FX12-5 | | | | | | | | | | | | | | | | | | | | | | | 5 |
| *Lactobacillus crispatus* clone FX32-3 | | | | | | | | | | | | | | | | | | | | | | | 0 |
| *Lactobacillus crispatus* clone FX36-3 | | | | | | | | | | | | | | | | | | | | 22 | | | 5 |
| *Lactobacillus crispatus* strain LAB32 | | | | | | | | | | | 15 | | | | | | | | | | | | 5 |
| *Lactobacillus crispatus* strain TL13 | | | | | | | | | | | | | | 12 | | | | 28 | | | | | 5 |
| *Lactobacillus crispatus* strain ZDY35b | | | | | | | | | | | | | 12 | | | | | | | | | 25 | 14 |
| *Lactobacillus jensenii* C72 | | | | | | | | | | | | | | | | | | | | | | | 0 |
| *Staphylococcus*, all species | 48 | 35 | 38 | 63 | 9 | | | 43 | 82 | 22 | 57 | 60 | 68 | 78 | 56 | 83 | 25 | 70 | 25 | 72 | 15 | 50 | 77 |
| *Staphylococcus aureus* | 48 | 35 | | 63 | 19 | 32 | | 43 | 82 | | 57 | 60 | 68 | 78 | | 83 | | 70 | 25 | 72 | | | 23 |
| *Staphylococcus aureus* FD42 | | | | | | | | | | | | | | | | | | | | | | | 14 |
| *Staphylococcus aureus* strain iZBN11 | | | | | | | | | | | | | | | | | 25 | | | | 15 | | 9 |
| *Staphylococcus aureus* strain I65 | | | | | | | | | | | | | | | | | | | | | | | 5 |
| *Staphylococcus aureus* strain LA14 | | | | | | | | | | 22 | | | | 78 | | | | | | | | | 5 |
| *Staphylococcus aureus* clone MT10B_A04 | | | | | | | | | | | | | | | 56 | | | | | | | 50 | 14 |
| *Staphylococcus aureus* strain YT-2 (96% match) | | | | | | | | | | | | | | | | | | | 25 | | | | 5 |
| *Staphylococcus haemolyticus* strain N11 | | | | | | | | | | | | | | | | | | | | | | | 5 |
| *Staphylococcus epidermidis* | | | | | 50 | | | | | | | | | | | | | | | | | | 18 |
| *Bacillus*, all species | | | 38 | | 16 | 32 | 2 | | 18 | 15 | 17 | | | 12 | | | 75 | | | 2 | 54 | | 50 |
| *Bacillus* sp. A12 | | | | | 16 | 32 | | | | 15 | | | | 12 | | | 75 | | | 2 | 54 | | 9 |
| *Bacillus* sp. BY143(A)Ydz-ds (93% match) | | | | | | | | | | | | | | | | | | | | | | | 5 |
| *Bacillus* sp. CPB 8 | | | | | | | | | | | | | | | | | | | | | | | 5 |
| *Bacillus* sp. GNA22 | | | | | | | | | | | | | | | | | | | | | | | 0 |
| *Bacillus* sp. HPC 1303 | | | | | | | | | | | | | | | | | | | | | | | 5 |
| *Bacillus* sp. RG1 | | | | | | | 2 | | | | | | | | | | | | | | | | 5 |
| *Bacillus* sp. RG4 (96% match) | | | | | | | | | | | | | | | | | | | | | | | 18 |
| Broad-Range 16S rDNA PCR clone | | | | | | | 35 | | | | | | | | | | | | | | | | |
| Bacilli bacterium clone MS145A1_G04 (96% match) | | | | | | | | | | | 10 | | | | | | | | | | | | 0 |
| *Bacillus cereus* | | | | | | | | | | | | | | | | | | | | | | | 5 |
| *Bacillus subtilis* strain WXZ-5 | | | | | | | | | | | 10 | | | | | | | | | | | | 0 |
| *Escherichia*, all species | | | | | | | | | | 15 | | | | | 8 | | | | | | | | 9 |
| *E. coli* | | | | | | | | | | 15 | | | | | 8 | | | | | | | | 9 |
| *Escherichia coli* str. K12 | | | | | | | | | | | | | | | | | | | | | | | 5 |
| *Escherichia fergusonii* | | | | | | | | | | | | | | | | | | | | | | | 0 |
| *Escherichia* sp. EMB 210 | | | | | | | | | | | | | | | | | | | | | | | 0 |
| *Corynebacterium*, all species | | | | | | | | | | | | 3 | | | | | | | | | | 10 | 18 |
| *Corynebacterium mastitidis* | | | | | | | | | | | | 3 | | | | | | | | | | | 5 |
| *Corynebacterium* sp. clone T0079 (95% match) | | | | | | | | | | | | 3 | | | | | | | | | | | 5 |

TABLE 3b-continued

Bacteria identified by broad range 16S rDNA PCR (>97% match) in urine of women during pregnancy. Matching <97% is shown as (value).

| Bacteria identified | Patient number | | | | | | | | | | | | | | | | | | | | | | |
|---|---|---|---|---|---|---|---|---|---|---|---|---|---|---|---|---|---|---|---|---|---|---|---|
| | 1 | 3 | 5 | 8 | 9 | 11 | 17 | 18 | 20 | 22 | 32 | 33 | 34 | 35 | 38 | 39 | 50 | 61 | 63 | 67 | 69 | 87 | |
| Number of clones analyzed | 100 | 100 | 100 | 100 | 100 | 100 | 100 | 100 | 100 | 100 | 100 | 100 | 60 | 60 | 60 | 100 | 100 | 60 | 100 | 60 | 100 | 100 | |
| Corynebacterium sp. R603 | | | | | | | | | | | | | | | | | | | | | | | 5 |
| Corynebacterium tuscaniense strain ISS-5309 | | | | | | | | | | | | | | | | | | | | | | 10 | 5 |
| Corynebacterium xerosis | | | | | | | | | | | | | | | | | | | | | | | 0 |
| Streptococcus, all species | | | | | | | | | | | | | | | | | | | | | | | 14 |
| Streptococcus | | | | | | | | | | | | | | | | | | | | | | | 0 |
| Streptococcus anginosus strain ChDC YA12 | | | | | | | | | | | | 6 | 2 | | | | | | | | | | 5 |
| Streptococcus anginosus clone UR062 | | | | | | | | | | | | | 2 | | | | | | | | | | 5 |
| Streptococcus anginosus strain VAMC5302 | | | | | | | | | | | | 6 | | | | | | | | | | | 5 |
| Streptococcus intermedius strain TG14 (96% match) | | | | | | 35 | | | | | | | | | | | | | | | | | 0 |
| Streptomyces, all species | | | | | | | | | | | | | | | | | | | | 2 | | 5 | 5 |
| Streptomyces sp. SC-13 | | | | | | | | | | | | | | | | | | | | 2 | | 5 | 5 |
| Streptomyces sp. SD-Z | | | | | | | | | | | | | | | | | | | | | | | 0 |
| Streptomyces sp. SX-3 | | | | | | | | | | | | | | | | | | | | | | | 9 |
| Pseudomonas, all species | | | | | | | | | | | | | | 10 | | | | 3 | | | | | 5 |
| Pseudomonas acephalitica (96% match) | | | | | | | | | | | | | | 10 | | | | 3 | | | | | 5 |
| Pseudomonas fulva | | | | | | | | | | | | | | | | | | | | | | | 0 |
| Pseudomonas fluorescens | | | | | | | | | | | | | | | | | | | | | | | 0 |
| Pseudomonas sp. 5S2.A12 | | | | | | | | | | | | | | | | | | | | | | | 0 |

Types of Bacteria and Dominant Species

In total, 79 different bacterial species were found. In Table 3, an overview is given. For the majority of analysis, the match between the obtained DNA sequence and the species-specific sequence in the BLAST databank exceeded 97%. Lower matching percentages are indicated in the table. Most species were found in only a few samples. Table 4 depicts the frequency with which bacterial species were found.

TABLE 4

Number of species present in one or more samples.

| | | | | | N samples | | | | | | |
|---|---|---|---|---|---|---|---|---|---|---|---|
| | 1 | 2 | 3 | 4 | 5 | 8 | 9 | 11 | 13 | 26 | 58 | 75 |
| N species | 49 | 12 | 3 | 3 | 2 | 1 | 2 | 3 | 1 | 1 | 1 | 1 |

N samples = Number of samples in which a specific species was present
N species = Number of species for which N samples applies (thus 49 species occurred in only 1 sample while 1 species occurred in 75 samples)

Minor Species

Most species were present as less than 10% of the population of only one woman and often in only one sample. In the pregnant group, 19 species were found at both time points (not necessarily in the same woman), 16 were unique for the first sample and 18 for the second sample. In the not pregnant group, 16 bacterial species occurred in both samples, 14 were unique for the first sample and 25 for the second sample. There were no unique bacterial species for the four different sample groups (not pregnant, pregnant, before failed IVF/ICSI, after failed IVF/ICSI).

Major Species

Five species occurred in all four sample groups. *Lactobacillus crispatus* and *Staphylococcus aureus* were present in the majority of all samples. *E. coli*, *Streptomyces* sp. and uncultured bacterium isolate CH96Fc_H10 were present in fewer samples but also in all four groups.

Dominant Species (Largest Fraction of the Total Population)

The average percentage occupied by a dominant species for the four sample groups was, respectively, 67±16% (first sample pregnant group, range 48% to 100%), 59±18% (second sample pregnant group, range 22% to 88%), 56±15% (first sample not pregnant group, range 20% to 100%) and 57±17% (second sample not pregnant group, range 18% to 100%). An overview of the dominant species is given in Table 5.

TABLE 5

Dominant species (18% to 100%)

| Pregnant Group | | | Not pregnant group | | |
|---|---|---|---|---|---|
| No. | first sample | second sample | No. | first sample | second sample |
| 10 | Lc | Sa | 6 | Sa | Sa |
| 4 | Lc | Lc | 6 | Lc | Lc |
| 2 | Lc | B RG4 | 2 | Lc | Sa |
| 1 | Lc | B CPB8 | 2 | Li | Li |
| 1 | Lc | Msb | 1 | Lcu | Lcu |
| 1 | Lc | S | 1 | Bc | Lc |
| 1 | Lj | B RG4 | 1 | Cc | Cc |
| 1 | Lj | Sa | 1 | UbB | UbE |
| 1 | B RG4 | B RG4 | | | |

Lc = *Lactobacillus crispatus*, Lcu = *Lactobacillus curvatus* clone B225, Li = *Lactobacillus iners*, Lj = *Lactobacillus jensenii* isolate C72, Sa = *Staphylococcus aureus*, B RG4 = *Bacillus* sp. RG4, Bcpb = *Bacillus* sp. CPB 8, Msb = Marine sediment bacterium ISA-3195, S = *Sphingomonas* sp. FL13-1-1, Cc = *Clostridium crispatus* cTPY-17, Bc = *Bacillus clausii* strain za-w-3, UbB = Uncultured bacterium clone Bermudas8-E3, UbE = Uncultured bacterium clone E67BE-207

In the pregnant group, various strains of *Lactobacillus* were the dominant species in 21 of the 22 samples taken at the first time point and in four samples taken during pregnancy. During pregnancy, *Staphylococcus aureus* was the most frequent dominant species. In 5 of the 22 women, the dominant species was identical for both samples.

In the not pregnant group, the dominant species in the first sample was a *Lactobacillus* species for 11 out of 20 women. In six samples, it was *Staphylococcus aureus*. The dominant species was the same in both samples for 16 out of the 20 women.

Based on the type of dominant species, the bacterial population appears stable in the failed IVF procedure (no effect of the IVF procedure) and subject to strong changes during pregnancy.

Specific Changes in Bacterial Population During Pregnancy and after IVF.

The shifts in abundance of bacterial species that occur during pregnancy are mainly a decrease of *Lactobacillus* species from 62±21% to 18±16% ($p<0.0001$), and increase in *Staphylococcus* species from 7±11% to 41±29% ($p<0.0001$).

In the not pregnant group, the abundance in the first versus the second sample did not change for both *Lactobacillus* species, 46±24 versus 40±27, and *Staphylococcus* species, 27±22 versus 32±25.

For the comparison above, the seven women who were not pregnant during collection of the second sample but did become pregnant at some other time point after collection of the first sample were assigned to the not pregnant group. Four of the 7 had no *Staphylococcus* in their first sample. Two had a high presence of *Staphylococcus* and became pregnant in the second or third year of follow-up (one had a miscarriage; one had a miscarriage followed by a successful spontaneous pregnancy after two years). The seventh woman had a high presence of *Staphylococcus*, a failed ICSI following the failed first IVF attempt and then became spontaneously pregnant within 1 year (miscarriage).

Relation of Bacterial Population to Previous UTI or Antibiotics Use.

Of the pregnant group, 5 women (23%) reported having had a UTI in the past and 2 (9%) had recently used antibiotics. Of the not pregnant group, 9 women (45%) had a UTI previously and 5 (25%) had recently used antibiotics. The differences were statistically not significant. The composition of the bacterial populations in the women who reported a previous UTI or use of antibiotics did not differ significantly from that in the other women of their respective groups.

Bacterial Population Before IVF/ICSI Versus the Outcome of the IVF/ICSI

The urine obtained before the IVF/ICSI procedure contained more *Staphylococcus* species (2722% versus 7±11%, $p<0.001$) and less *Lactobacillus* species (46±24% versus 62±21%, $p<0.001$) for the not pregnant group compared to the pregnant group.

Major Causes of UTI and Vaginal Infection in Pregnant and Non-Pregnant Women

In 2009, a total number of 599 urine cultures and 206 vaginal smear cultures were performed for women attending the Maternity hospital in Erbil (Kurdistan region, Iraq). In Table 6, the results are shown for women who were, respectively, pregnant or not pregnant. In women who are not pregnant, *E. coli* was found in 44% (70/158) of all positive urine cultures and *Staphylococcus aureus* in 22% (35/158). In pregnant women, *E. coli* was found in 21% (75/350) and *Staphylococcus aureus* in 50% (175/350).

For vaginal smear, *E. coli* was the pathogen found in 29% (24/84) and *Staphylococcus* in 29% (25/84) of all positive smears in women who were not pregnant. For pregnant women, the numbers were 38% (28/74) for *E. coli* and 49% (36/74) for *Staphylococcus aureus*. For urine and to a lesser extant for vaginal smear, there was a shift toward increased presence of *Staphylococcus aureus* during pregnancy ($p<0.001$) and decreased presence of *E. coli* ($p<0.001$).

TABLE 6

| | total | neg. | pos. | pseudo. | E coli | Kleb. | Staph. a | Enterob. | Portus sp. | Streptoc. |
|---|---|---|---|---|---|---|---|---|---|---|
| | | | | | Urine | | | | | |
| Pregnant | 389 | 39 | 350 | 0 | 75 | 17 | 175 | 69 | 11 | 3 |
| Not pregnant | 210 | 52 | 158 | 1 | 70 | 4 | 35 | 39 | 6 | 3 |
| | | | | | Vaginal smear | | | | | |
| Pregnant | 122 | 48 | 74 | 0 | 28 | 4 | 36 | 3 | 1 | 2 |
| Not pregnant | 94 | 10 | 84 | 0 | 24 | 14 | 25 | 18 | 3 | 0 |

Pseudo. = pseudomonas species,
Kleb. = Klebsiella species,
enterob. = enterobacter species,
Streptoc. = streptococcus species.

Prediction Models for the Chance of Success of IVF/ICSI

The models were built by binomial regression analysis with input of the bacterial species identified in the first urine sample (before IVF/ICSI, n=42). Lactobacillus species and Staphylococcus species contributed significantly to the model. The best prediction of pregnancy after the first IVF/ICSI was obtained with the model Y=0.030*% Lactobacillus−0.057*% Staphylococcus−1.031. When patient 58 was assigned to the pregnant group (she became pregnant around the time the first sample was collected), the equation became Y=0.034*% Lactobacillus−0.064*% Staphylococcus−0.668 and the % correctly predicted pregnant increased from 86% to 96%. For the first year prediction, the equation was Y=0.051*% Lactobacillus−0.056*% Staphylococcus−1.053. Table 7 shows the cross table values for the first IVF/ICSI attempt model and the 1-year period model. In the 1-year period model, multiple IVF/ICSI attempt were made.

TABLE 7

| | | Predicted | | | | | |
|---|---|---|---|---|---|---|---|
| | | First attempt | | | 1 year | | |
| | | not pregnant | pregnant | % correct | not pregnant | pregnant | % correct |
| observed | not pregnant | 16 | 4 | 80 | 12 | 4 | 75 |
| | pregnant | 3 | 19 | 86 | 2 | 24 | 92.3 |

The ROC curves for the two models show that from the area under the curve (0.819, first attempt and 0.901, 1 year) it appears that pregnancy within 1 year could be predicted best. In this 1-year prediction, the cause of infertility was male for three out of the four false positive predictions and one of the two false negative predictions. The cause was unknown for one out of four false positive predictions and one of the two false negative predictions.

To test if a relation exists between the cause of the infertility and the predictive power of the model, the women were subdivided into known cause of infertility (n=30) and unknown cause of infertility (n=12) (Table 8).

TABLE 8

| | | 1 year prediction | | | | | |
|---|---|---|---|---|---|---|---|
| | | Known cause | | | Unknown cause | | |
| | | not pregnant | pregnant | % correct | not pregnant | pregnant | % correct |
| observed | not pregnant | 6 | 4 | 60 | 6 | 0 | 100 |
| | pregnant | 1 | 24 | 96 | 1 | 5 | 83 |

For the women who were not pregnant during collection of the second sample, n=20, new IVF/ICSI attempts were started. The 1-year model was used to predict on the basis of that second sample if these women would become pregnant by these new attempts within the next 12 months. Four women became pregnant in that period (patients 10, 14, 19 and 58). Table 9 shows actual outcome versus outcome predicted by the model. The prediction that the new attempts would not result in pregnancy was correct in 14/15 cases (93%).

TABLE 9

|  |  | Predicted | | |
|---|---|---|---|---|
|  |  | not pregnant | pregnant | % correct |
| observed | not pregnant | 14 | 2 | 88 |
|  | pregnant | 1 | 3 | 75 |

When the model was applied to the urines obtained at the 16$^{th}$ week of pregnancy, the model predicted that none of these women would become pregnant from a subsequent IVF/ICSI procedure.

Leave-One-Out Model

To validate the prediction model, a leave-one-out procedure was applied. In this procedure, a model was built from the data of 41 patients and this model was applied to the urine data from the patient that was left out to predict if this patient would become pregnant or not within 1 year of starting with IVF/ICSI. The results (Table 10) completely match those obtained with the total group of 42 (Table 7).

TABLE 10

|  |  | Predicted | | |
|---|---|---|---|---|
|  |  | not pregnant | pregnant | % correct |
| observed | Not pregnant | 12 | 4 | 75 |
|  | pregnant | 2 | 24 | 92 |

In the validation group, the model correctly predicted 24 of 28 pregnancies and 12 of 16 failures (Table 10).

Comparison to Existing Model [5]

In the model from Nelson, the individual chance for a live birth is predicted on the basis of age, duration of child-wish and several other clinical parameters. The data was entered for the study group into the model and its outcome was compared for the women with observed live birth within 1 year versus the women without a live birth, (Table 11). The predicted chance did not differ for both groups (p=0.18, unpaired t-test).

TABLE 11

|  |  | % Chance for live birth (Nelson model) | |
|---|---|---|---|
|  |  | Average | s.d. |
| observed | not pregnant | 27 | 9 |
|  | pregnant | 23 | 11 |

Example 2 qPCR for *Staphylococcus* Species and *Lactobacillus* Species

Since the prediction model as shown in Example 1 only uses data on the presence of *Lactobacillus*, *Staphylococcus* and total number of bacteria present, it was decided to develop a qPCR procedure specifically directed to measure those three values.

In a urine sample, a PCR is performed with the general primer set (EUB-R, EUB-L). The product of this PCR is a mixture of 16S rDNA derived from all bacteria in the urine, and thus representative for the total number of bacteria.

Subsequently, on this total mixture, a qPCR is performed with three primer sets, a general primer set, a primer set specific for (multiple types of) *Lactobacillus* and a primer set specific for (multiple types of) *Staphylococcus*.

The total DNA content of the initial PCR product is measured via a nanodrop assay. The DNA in this analysis almost totally is comprised of 16S rDNA. On the basis of this nanodrop analysis, the total amount of DNA in each assay can be kept the same.

The general primer will react with all 16S rDNA fragments and thus will produce the CT value that defines 100% of the bacterial population. The general primer set will also be tested on a dilution series of the initial PCR product (1, 0.8, 0.6, 0.4, 0.2, 0.1). This dilution series will result in a CT value that matches with an amount of DNA of about 80%/a, 60%, 40%, 20% and 10%, respectively, of the total.

The qPCR assays with the specific primer sets will result in a CT value that is equal to the CT value obtained with the general primer set (if the population only contains one species) or higher (if the tested species is only part of the total population). On basis of the dilution series, it can be determined which percentage matches this specific CT value.

*Staphylococcus aureus* primer set (as published in "Molecular analysis of bacterial population structure and dynamics during cold storage of untreated and treated milk," E. A. Rasolofo, D. St-Gelais, G. LaPointe, and D. Roy, *Int. J. Food Microbiol.* 2010 Mar. 31; 138(1-2): 108-18. Epub 2010 Jan. 20):

```
Forward (nt 61) primer
5'-GAGTAACACGTGGATAACCTACCTATAAGAC-3'
(SEQ ID NO: 1)

Reverse (nt 241) primer
5'-GCATCGTTGCCTTGGTAAGC-3'  (SEQ ID NO: 2)
```

Fragment Size 201 bp

*Lactobacillus crispatus* primer set (as published in "Quantitative PCR Assessments of Bacterial Species in Women with and without Bacterial Vaginosis," Marcela Zozaya-Hinchliffe, Rebecca Lillis, David H. Martin, and Michael J. Ferris, *J. Clin Microbiol.* 2010 May; 48(5):1812-1819; published online 2010 Mar. 19. doi: 10.1128/JCM.00851-09. PMCID: PMC2863870).

```
Forward primer
GATTTACTTCGGTAATGACGTTAGGA (SEQ ID NO: 3)

Reverse primer
AGCTGATCATGCGATCTGCTTTC (SEQ ID NO: 4)
```

The invention claimed is:

1. A method for determining the composition of a bacterial population in the urinary tract of a subject comprising the steps of
   a. obtaining a urine or vaginal sample from the subject;
   b. determining the amount of the bacteria belonging to the group of Lactobacillae, in the sample;
   c. determining the amount of *Staphylococcus* bacteria in the sample; and
   d. determining the total amount of bacteria present in said sample,
wherein the measurement of the amount of Lactobacillae, *Staphylococcus*, and total bacteria are performed by polymerase chain reaction (PCR), quantitative PCR (qPCR), or mass spectrometry.

2. The method of claim 1, wherein the subject is undergoing or is eligible for an artificial insemination method, such as in vitro fertilization (IVF) or intra-cytoplasmatic sperm injection (ICSI).

3. The method of claim 1, wherein the group of Lactobacillae comprises the *Lactobacillus* species *Lactobacillus crispatus*.

4. The method of claim 1, wherein the *Staphylococcus* bacteria comprises *Staphylococcus aureus*.

5. The method of claim 1, wherein the amount of *Staphylococcus* is determined by using the primers 5'-GAGTAACACGTGGATAACCTACCTATAAGAC-3' (SEQ ID NO: 1) and 5'-GCATCGTIGCCTIGGTAAGC-3' (SEQ ID NO: 2).

6. The method of claim 1, wherein the amount of bacteria belonging to the group of Lactobacillae is determined by using the primers 5'-GATTIACTTCGGTAATGACGTTAGGA-3' (SEQ ID NO: 3) and 5'AGCTGATCATGCGATCTGCTITC-3' (SEQ ID NO: 4).

7. The method of claim 1, wherein the vaginal sample is a vaginal smear.

8. The method of claim 1, wherein the determining of the amount of the bacteria is performed by MALDI-TOF mass spectrometry.

9. The method of claim 1, wherein the urine sample is a midstream urine sample.

* * * * *

SEQUENCE LISTING

<160> NUMBER OF SEQ ID NOS: 19

<210> SEQ ID NO 1
<211> LENGTH: 31
<212> TYPE: DNA
<213> ORGANISM: Artificial Sequence
<220> FEATURE:
<223> OTHER INFORMATION: primer

<400> SEQUENCE: 1
gagtaacacg tggataacct acctataaga c                       31

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gcatcgttgc cttggtaagc                                    20

<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
gatttacttc ggtaatgacg ttagga                             26

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
agctgatcat gcgatctgct ttc                                23

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
agagtttgat cctggctcag                                    20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ggttaccttg ttacgactt                                     19

<210> SEQ ID NO 7
<211> LENGTH: 23
<212> TYPE: DNA
<213> ORGANISM: Artificial Sequence

```
<220> FEATURE:
<223> OTHER INFORMATION: primer

<400> SEQUENCE: 7
taaaactyaa akgaattgac ggg                                              23

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
actgctgcsy cccgtaggag tct                                              23

<210> SEQ ID NO 9
<211> LENGTH: 15
<212> TYPE: DNA
<213> ORGANISM: Artificial Sequence
<220> FEATURE:
<223> OTHER INFORMATION: primer

<400> SEQUENCE: 9
yaacgagcgc aaccc                                                       15

<210> SEQ ID NO 10
<211> LENGTH: 15
<212> TYPE: DNA
<213> ORGANISM: Artificial Sequence
<220> FEATURE:
<223> OTHER INFORMATION: primer

<400> SEQUENCE: 10
gggttgcgct cgttg                                                       15

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
gactcctacg ggaggcwgca g                                                21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ccgtcaattc ctttragttt                                                  20

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
ggattagata ccctggta                                                    18
```

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gactaccagg gtatctaatc                                         20

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
gtgccagcmg ccgcggtaa                                          19

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
gtattaccgc ggctgctgg                                          19

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ctttacgccc atttaatccg                                         20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
agagtttgat cctggttcag                                         20

<210> SEQ ID NO 19
<211> LENGTH: 20
<212> TYPE: DNA
<213> ORGANISM: Artificial Sequence
<220> FEATURE:
<223> OTHER INFORMATION: primer 16S rDNA

<400> SEQUENCE: 19
taatacgact cactataggg                                         20